(12) United States Patent
Qureshi et al.

(10) Patent No.: US 9,375,522 B2
(45) Date of Patent: Jun. 28, 2016

(54) EXTRADURAL INFUSION SUCTION SYSTEM AND METHOD TO DRAIN FLUID COLLECTION IN THE EXTRADURAL SPACE OF SPINAL CORD

(76) Inventors: Adnan Iqbal Qureshi, Minneapolis, MN (US); Muhammad Fareed Khan, Blaine, MN (US); Stanley H. Kim, Austin, TX (US)

( * ) Notice: Subject to any disclaimer, the term of this patent is extended or adjusted under 35 U.S.C. 154(b) by 285 days.

(21) Appl. No.: 13/418,515

(22) Filed: Mar. 13, 2012

(65) Prior Publication Data

US 2012/0253266 A1 Oct. 4, 2012

Related U.S. Application Data

(60) Provisional application No. 61/516,421, filed on Apr. 4, 2011.

(51) Int. Cl.
*A61M 1/00* (2006.01)
*A61M 3/02* (2006.01)
*A61B 17/34* (2006.01)

(52) U.S. Cl.
CPC .......... *A61M 1/0084* (2013.01); *A61B 17/3401* (2013.01); *A61M 2210/1003* (2013.01)

(58) Field of Classification Search
CPC ............ A61M 3/0283; A61M 1/0058; A61M 1/0023; A61M 1/008; A61M 1/0084; A61M 2210/1003; A61M 17/3401
USPC ......... 604/27–28, 30, 35, 39, 40, 43–44, 317, 604/540–541, 543
See application file for complete search history.

(56) References Cited

U.S. PATENT DOCUMENTS

| | | | |
|---|---|---|---|
| 1,211,928 A * | 1/1917 | Fisher | 604/40 |
| 3,426,759 A | 2/1969 | Smith | |
| 3,771,527 A * | 11/1973 | Ruisi | 604/43 |
| 4,468,216 A * | 8/1984 | Muto | 604/43 |
| 4,737,146 A | 4/1988 | Amaki et al. | |
| 5,002,528 A * | 3/1991 | Palestrant | 604/28 |
| 5,447,494 A | 9/1995 | Dorsey, III | |
| 5,536,242 A | 7/1996 | Willard et al. | |
| 7,022,109 B1 * | 4/2006 | Ditto | 604/158 |
| 7,150,737 B2 | 12/2006 | Purdy et al. | |
| 7,455,666 B2 | 11/2008 | Purdy | |
| 2002/0058904 A1 | 5/2002 | Boock et al. | |
| 2006/0184098 A1 | 8/2006 | Barnitz et al. | |
| 2009/0227851 A1 | 9/2009 | Radojicic | |
| 2009/0281485 A1 * | 11/2009 | Baker et al. | 604/35 |
| 2009/0292276 A1 | 11/2009 | Nash et al. | |

OTHER PUBLICATIONS

S. Grewal, Epidural abscesses, Jan. 23, 2006, British Journal of Anaesthesia, 96 (3), 292-302.*

* cited by examiner

*Primary Examiner* — Theodore Stigell
(74) *Attorney, Agent, or Firm* — Nikolai & Mersereau, P.A.; C. G. Mersereau

(57) ABSTRACT

A minimally invasive method of and apparatus for aspirating purulent material from an epidural abscess, or the like, in a patient includes a dual concentric catheter system having an inner infusion catheter and an outer suction catheter, the infusion catheter able to be advanced relative to and beyond the suction catheter. The catheter system is introduced into the extradural space through percutaneous entry and advanced to an epidural abscess of interest. Infusion is used to dislodge purulent material ahead of the infusion catheter toward side openings in the suction catheter where it is aspirated.

7 Claims, 8 Drawing Sheets

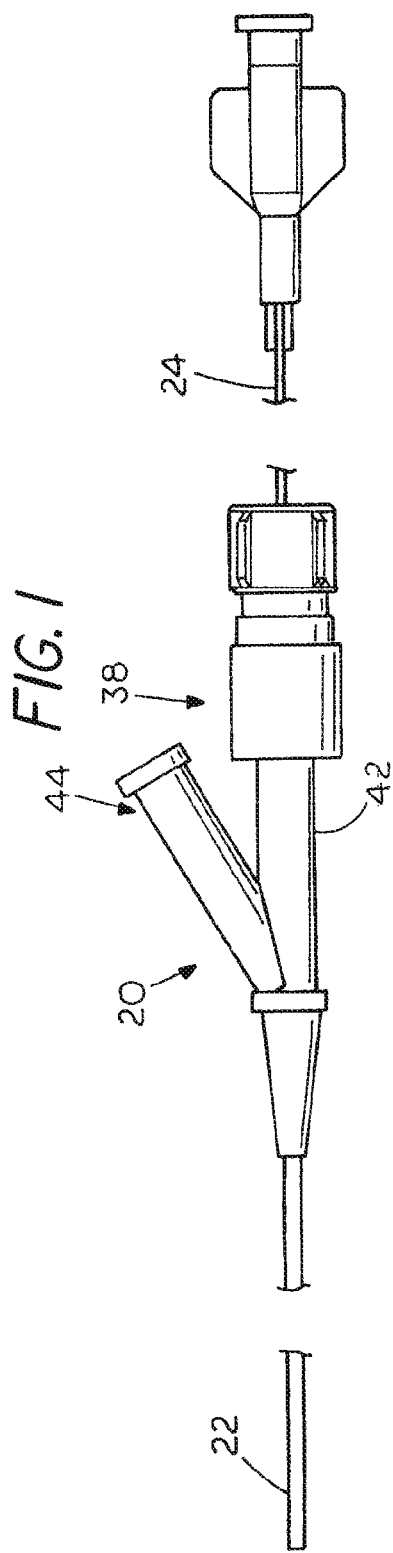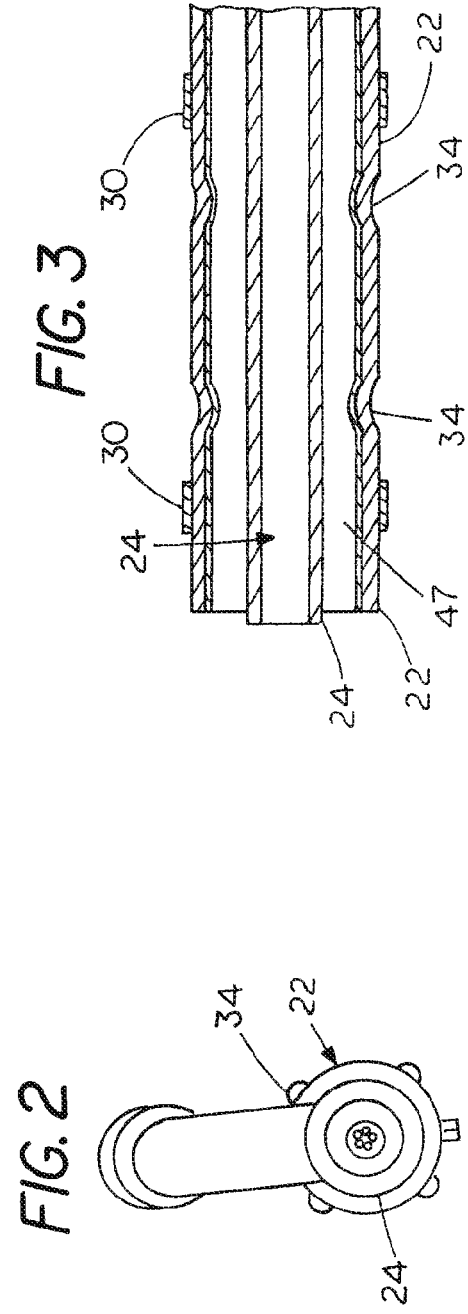

EXTRADURAL INFUSION SUCTION SYSTEM AND METHOD TO DRAIN FLUID COLLECTION IN THE EXTRADURAL SPACE OF SPINAL CORD

CROSS-REFERENCED TO RELATED APPLICATIONS

This application is a non-provisional application of Application No. 61/516,421, filed Apr. 1, 2011, and claims priority from that application which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention relates generally to nonsurgical procedures and devices and, more particularly, to a method and a minimally invasive infusion/suction catheter system for removing collected epidural fluid related to epidural abscesses and other etiologies surrounding the spinal cord to treat infection and relieve external compression.

II. Related Art

In humans, the vertebral column is a column usually consisting of 33 vertebrae, the sacrum, intervertebral discs, and the coccyx situated in the dorsal aspect of the torso. The vertebral canal follows the different curves of the column, it is large and triangular in those parts of the column which enjoy the greatest freedom of movement, such as the cervical and lumbar regions; and is small and rounded in the thoracic region, where motion is more limited. The spinal cord is located inside the vertebral canal and extends from the foramen magnum down to the level of the first and second lumbar vertebrae (at birth, down to second and third lumbar vertebrae). The spinal cord is composed of 31 segments: 8 cervical (C), 12 thoracic (T), 5 lumbar (L), 5 sacral (S), and 1 coccygeal (Co), mainly vestigial. The spinal nerves comprise the sensory nerve roots, which enter the spinal cord at each level, and the motor roots, which emerge from the cord at each level which is formed by the foramina of the 7 cervical, 12 thoracic, 5 lumbar and 5 sacral vertebrae, which together form the spine. The conus medullaris is the cone-shaped termination of the caudal cord. The pia mater continues caudally as the filum terminale through the dural sac and attaches to the coccyx.

Within the vertebral canal, both spinal cord (CNS) and spinal roots (PNS) are enveloped by the meninges. Spinal dura mater is separated from the periosteum lining the vertebral canal by an extradural space that contains a variable amount of fat (in the cranial cavity, dura mater and periosteum merge so an extradural space does not exist). Three layers of meninges envelop the spinal cord and the roots of spinal nerves. The most superficial menix is dura mater. It is protective by virtue of its high collagen content. The space between spinal dura mater and periosteum lining the vertebral bone canal is called extradural space. The dura mater is expansile so the space can accommodate structures with diameter up to 0.06 to 0.07 inches. Arachnoid (arachnoid membrane) is thin and delicate, being composed of flattened fibrocytes and flimsy strands of collagen. In life, arachnoid contacts dura mater due to cerebrospinal fluid pressure within the subarachnoid space. Arachnoid trabeculae are delicate strands of arachnoid that traverse the subarachnoid space to join pia mater. Bilaterally, pia mater collagen is thickened to form denticulate ligaments. Processes of the ligaments periodically join dura mater and thus, within dura mater, the spinal cord is suspended by bilateral denticulate ligaments and thereby surrounded by protective cerebrospinal fluid within the subarachnoid space.

An epidural abscess is a localized collection of purulent material in the extradural space due to bacterial infection causing back pain, spinal cord compression, and systemic manifestations of infection (fever, leukocytosis). Spinal cord compression develops when the spinal cord is compressed by the abscess or other fluid collection. This condition is regarded as a medical emergency independent of its cause, and requires swift diagnosis and treatment to prevent long-term disability due to irreversible spinal cord injury. The present surgical procedure involves exposure of the extradural space to aspirate purulent material to relieve pressure on the spinal cord or the nerve roots. However, the process is extensive particularly when the epidural abscess involves multiple spinal segments and is associated with complications such as destabilization of vertebral bodies and lamina, or worsening of neurological deficits. Furthermore, open surgical removal may result in spread of infection along the surgical tract.

External compression of spinal cord by fluid collection in the extradural space most commonly due to epidural abscess remains a major cause of myelopathy. The external compression of the spinal cord leads to paraparesis, segmental sensory loss and urinary and fecal incontinence. As indicated above, an open surgical approach to alleviate the condition also has the undesirable risk of disseminating the infection in the surgical tract. If an open surgical approach is used, an epidural abscess that spreads over several spinal levels requires a large surgical exposure under general anesthesia. Because of this, a less risky, less invasive procedure has been sought to treat this type of condition.

In accordance with attempts at less invasive methods, epidural catheter devices have been developed including devices that may be able to inject and remove material by combining coaxial inner infusion and outer removal catheters such as shown in Amaki et al. (U.S. Pat. No. 4,737,146). However, that device has certain drawbacks, including an open distal infusion tip and inability to have the inner (infusion) catheter advanced beyond the outer catheter. Thus, it is difficult to maneuver and hard to separate infused material and material to be removed. A dual lumen spinal device is shown in Pub. U.S. Application 2006/0184098 A1 to Barnitz et al. and a dual lumen composite probe device is shown in U.S. Pat. No. 5,447,494 to Dorsey, III. Thus, while a variety of composite suction and irrigation probe and catheter devices have been proposed that are capable of invading the extradural space, there remains a need for a minimally invasive procedure using a more highly maneuverable and adjustable catheter system using various trajectories of flow between infusion and aspiration to more efficiently approach and remove epidural fluid collection related to epidural abscesses and other etiologies surrounding the spinal cord which are located in various compartments to treat infection and internal compression.

SUMMARY OF THE INVENTION

By means of the present invention, the above-described need is met by providing a minimally invasive method to deploy and operate a coaxial infusion-suction catheter system in the extradural space around the spinal cord. The infusion-suction catheter system can be introduced through a percutaneous needle puncture at lumbar interspace from a posterior approach. The process may be compared to a lumbar puncture and introduction of extradural leads (electrodes) for pain control. Thereafter, a flexible introducer wire is advanced through the percutaneously introduced needle under fluoroscopic guidance towards the cephalic direction. This is followed by advancing an introducer sheath over the guidewire, the introducer sheath containing a concentric infusion-suction catheter which is advanced along the extradural space to access an epidural abscess of interest using radiographic guidance. Flushing liquid is infused into the epidural abscess from openings in the distal portion of the infusion aspect of the catheter to dislodge purulent material that is aspirated through openings in the suction aspect of the infusion-suction catheter system until no more purulent material is observed in the aspirate. Thereafter the catheter system is withdrawn from the extradural space.

The infusion-suction catheter system includes an outer suction catheter and inner infusion catheter in concentric relation. The combined apparatus is designed to be introduced through the percutaneous approach over the wire after removal of the needle. The infusion-suction system may be advanced through the introducer needle and under fluoroscopic guidance through the anterior space between spinal cord and vertebral bodies and discs.

In the infusion-suction catheter system of the invention, the inner infusion catheter is separately maneuverable from the outer catheter and can be extended beyond the end of the outer catheter. The device includes spaced radio-opaque marker bands located on the distal portion of both the outer suction and inner infusion catheters. The inner infusion catheter is provided with a closed blunt distal nose or one which may be provided with a pressure driven closure valve and has a plurality of side infusion openings, preferably pairs of distal and proximal openings located close to the distal tip. The outer suction catheter has a plurality of openings through which material displaced by infusion can be aspirated.

The selected infusion-suction system can be advanced over a 0.014-inch guidewire and navigated to the site of epidural abscess. The infusion catheter is longer than the suction catheter allowing it to be moved easily beyond the end of the suction catheter. The infusion catheter can infuse normal saline or water within the collection of the purulent material with subsequent suction of displaced purulent material by the proximally placed suction catheter. Both the infusion system (connected to the external end of infusion catheter) and suction system (connected to the external end of suction catheter) can be programmed into various modes to allow controlled and titrated aspiration of abscess or other fluid collection.

BRIEF DESCRIPTION OF THE DRAWINGS

The invention is illustrated in the drawings in which like reference characters designate the same or similar parts throughout the same and in which:

FIG. 1 is a longitudinal view of an outer suction catheter demonstrating the proximal portion attached to a two-way Y connector, in which a central port provides access to an inner infusion catheter and an angulated port is designed to be connected to a suction pump;

FIG. 2 is a cross-sectional view through the device demonstrating the outer suction catheter and inner infusion catheter within the central lumen of outer suction catheter;

FIG. 3 is an enlarged distal end view of the device that is transected to demonstrate the relationship between outer suction catheter and inner infusion catheter. The distal end of the outer catheter includes four openings with a diameter of about 0.025 inches each. The figure also shows the radio-opaque markers on distal ends of outer suction catheter and inner infusion catheter that allow fluoroscopic assessment of the relative position of distal end of both catheters;

DETAILED DESCRIPTION

A. Definitions

Figure 4:
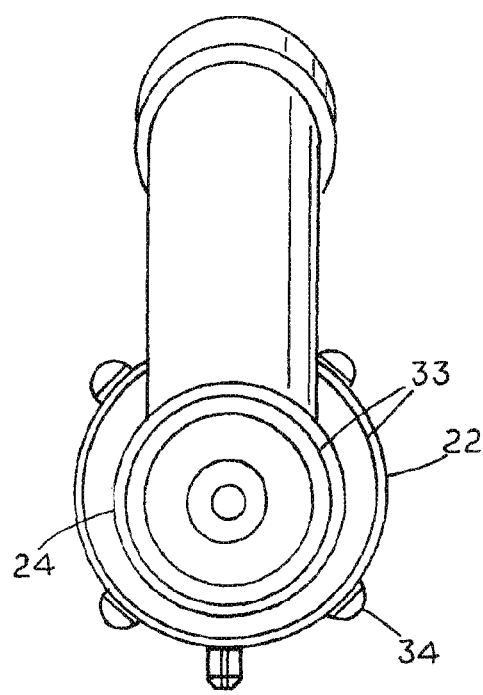
FIG. 4 is an enlarged cross-sectional view of the distal end of the device showing the outer suction catheter and circumferential placement of the four inlet openings and inner infusion catheter.
Figure 5:
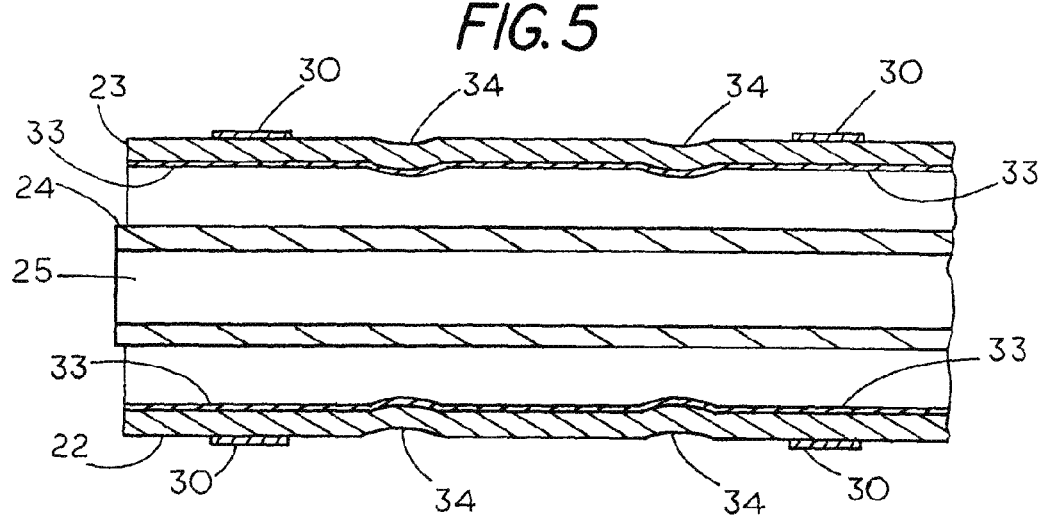
FIG. 5 is an enlarged distal end of the device that is transected to show the relative sizes of various components of the distal end of the device.
Figure 6:
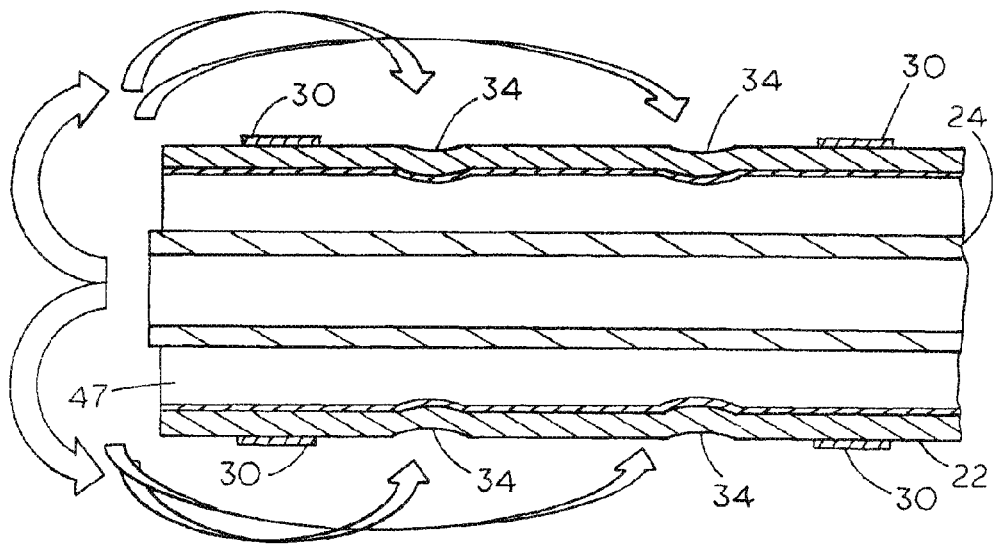
FIG. 6 is an enlarged view of the distal end of one embodiment of the device that is transected to show the synergistic function of outer suction catheter and inner infusion catheter.

The following list defines certain terms as used throughout the present specification:

1) "Extradural space"—The space between spinal dura mater and the periosteum lining the vertebral bone canal. The dura mater is expansile so the space can accommodate structures with diameter up to 0.06 to 0.07 inches.

2) "Epidural abscess"—A localized collection of purulent material in the extradural space due to bacterial infection causing back pain, spinal cord compression, and systemic manifestations of infection (fever, leukocytosis).

3) "Extradural drainage"—Surgical procedure involving exposure of the extradural space to aspirate purulent material to relieve pressure on the spinal cord or the nerve roots.

4) "insertion needle"—A 14-gauge needle of a class typically used for standard lumbar drain placements and insertion of extradural electrodes. The needle has an inner solid pointed needle and outer cannula with an angulated blunt tip. In use, the needle is placed through the intervertebral foramen penetrating through the skin, soft tissue, intervertebral space, supraspinous ligament, interspinous ligament and ligamentum flavum.

5) "Outer suction catheter"—The outer suction catheter of the invention is made of polyamide, preferably lined by polytetrafluoroethylene (PTFE) and is designed to have an external diameter of about 0.067 inches (inner diameter of about 0.055 inches) and length of about 80 cm. In a preferred embodiment, the distal end has a plurality, generally four openings, with a diameter of about 0.025 inches each. They are arranged as distal openings and proximal openings in which the distal openings are placed about 0.075 inches from the distal most end of the suction catheter. The proximal holes are placed about 0.15 inches from the distal end of the suction catheter. The proximal portion is attached to a two-way Y connector. The central port provides access to an infusion catheter and the angulated port is designed to connect the suction catheter to a suction pump.

6) "Suction pump"—The suction pump is one that can be programmed to a suction pressure of ~−5 to ~−30 cm of $H_2O$. The suction can be continuous or may be synchronized as desired with an associated infusion system to follow each infusion.

7) "Inner infusion catheter"—The distal portion of the inner infusion catheter of the invention is preferably made of 55D Pebax for flexibility and the remainder is preferably PTFE lined polyimide and is designed to have a length of about 100 cm. The outer diameter is about 0.026 inches and inner diameter is about 0.016 inches. The infusion catheter has a single lumen with a distal port and proximal port. The proximal port is connected to an infusion system that infuses liquid. Typically normal saline or water in a continuous or pulsatile spray mode. The distal end is designed to be placed within the abscess or fluid collection sought to be removed.

8) "Suction conduit"—The space between the outer suction catheter and inner infusion catheter which allows aspirated material to move from the distal openings into a suction bag connected to the angulated proximal end of the outer suction catheter. The diameter of the space may be about 0.029 inches.

9) "Infusion system"—The proximal port is connected to an infusion system that is designed to infuse normal saline or water in a continuous or pulsatile spray mode. The infusion system can be set to a particular volume (nominal range 1-5 cc per minute) and particular pressure (nominal range 10-30 cm of $H_2O$) at which the infusion will automatically discontinue.

10) "Guidewire"—A generally 0.014 inch guidewire made of nitinol or stainless steel with a length of about 150 cm that can be introduced through the central lumen of the infusion catheter for navigation or mechanical disruption of localized pockets of purulent material. A distal section of about 2 cm is flexible and can be shaped into an angulated curve. The distal end of the guidewire can be maneuvered from its proximal end outside of the infusion catheter.

11) "Pressure driven closure valve"—A valve placed at the distal end of the inner infusion catheter by providing a segment of about 2 mm that is made of polyurethane and collapsible and which will slow or stop the infusion process if the localized pressure in the vicinity of the distal end of the inner infusion catheter exceeds a given value, nominally 25 mm Hg.

B. Illustrative Embodiments

The following description details one or more embodiments of the device and associated procedures. These are intended as examples and are not intended to limit the scope of the inventive concepts. Other variations may occur to those skilled in the art that are within the scope of the invention.

Figure 7:
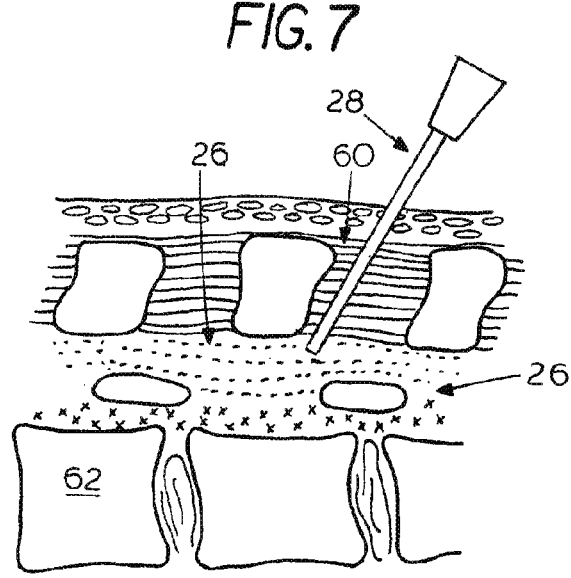
FIG. 7 illustrates the percutaneous introduction of needle into the extradural space through the skin, soft tissue, and ligamentum favum via the 2nd, 3rd or 4th intervertebral space.
Figure 8:
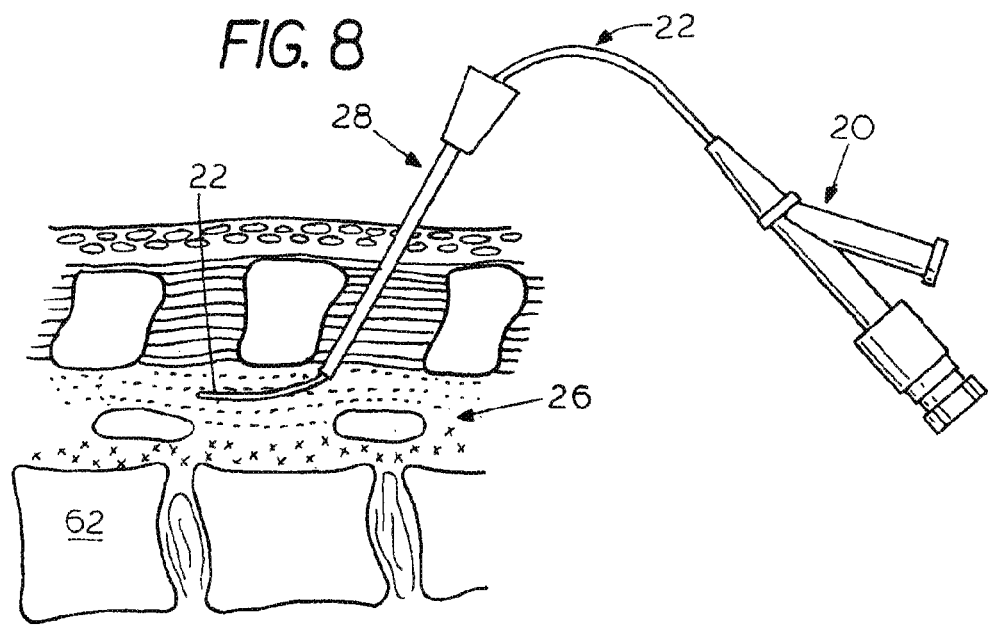
FIG. 8 illustrates the introduction of a drainage catheter through the needle into the extradural space in a longitudinal view also identifying the radio-opaque markers at a distal end portion of the device.
Figure 9:
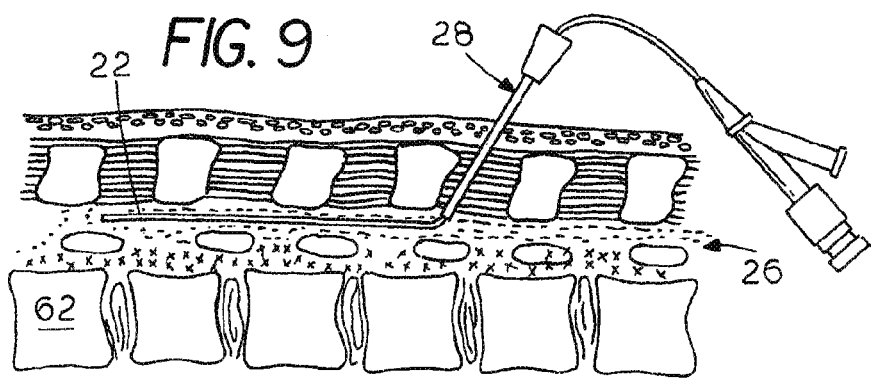
FIG. 9 is a lateral view illustrating the cephalad advancement of the device through the extradural space.
Figure 10:
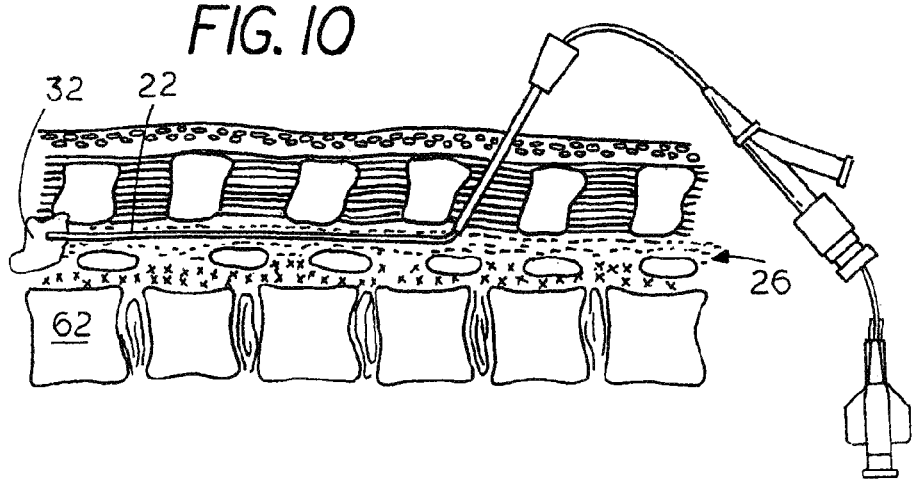
FIG. 10 is a lateral view showing the device entering the epidural abscess with the inner infusion catheter leading followed closely by the outer suction catheter.
Figure 11:
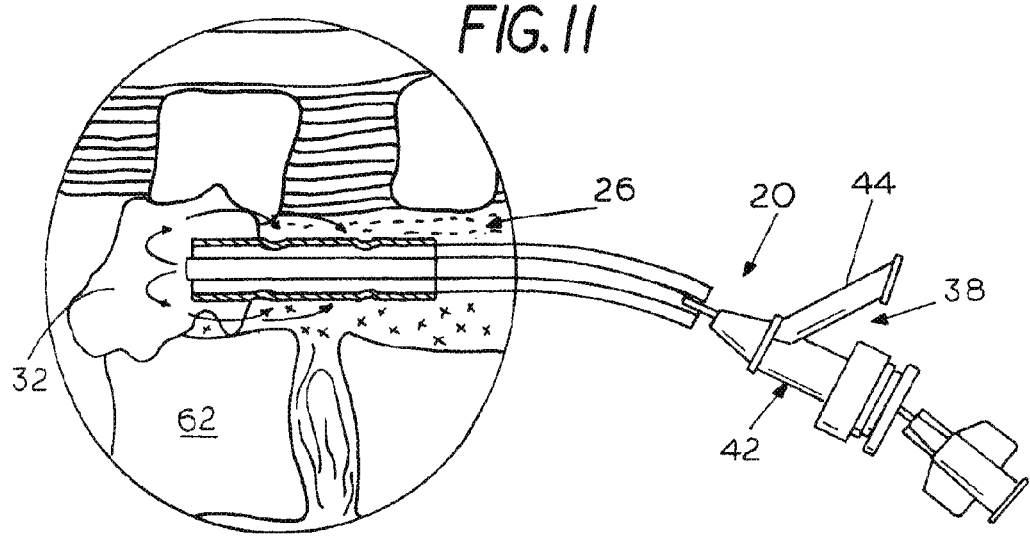
FIG. 11 is an enlarged longitudinal lateral view showing the infusion of saline by the inner infusion catheter and drainage of purulent material and infused solution through the four holes and lumen of the outer suction catheter.
Figure 12:
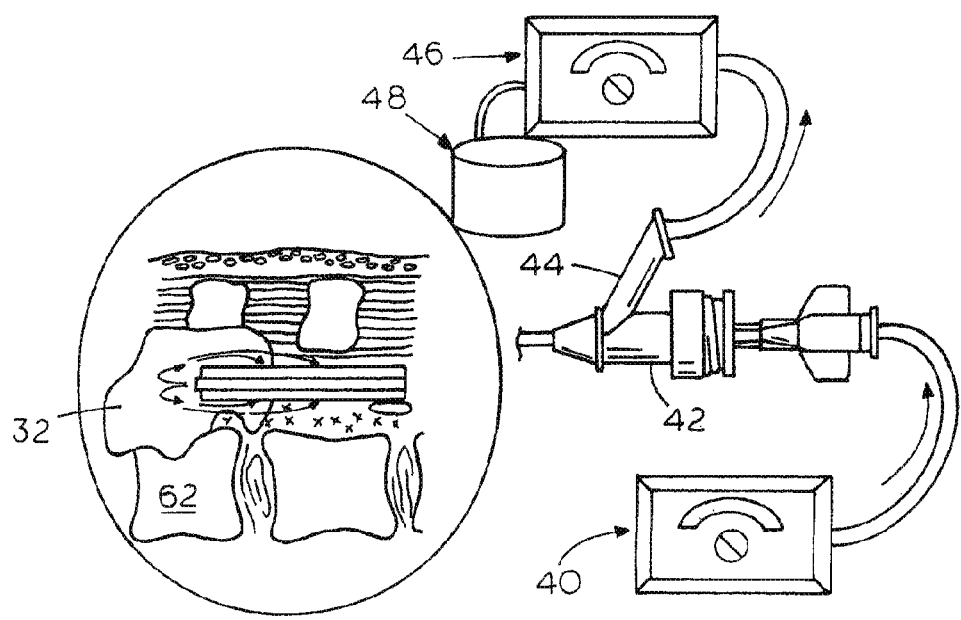
FIG. 12 is an enlarged longitudinal lateral broken view illustrating the connection of the angulated port to a suction pump and suction bag, and the connection of the inner infusion catheter with an infusion system.

Certain constituents of the device have been at least partially described in the definition section detailing the terms used. Referring first to FIGS. 1-6, generally, and initially to FIGS. 1 and 2, the device of the present invention shown generally at 20, includes an outer suction catheter 22 and inner infusion catheter 24 which can be introduced into the extradural space 26 (FIGS. 7-12) through an insertion needle 28 (FIGS. 7-9) within the vertebral canal under fluoroscopic guidance (FIG. 7). The device includes an assembly bands of radio-opaque markers 30 on the distal end of both catheters for visualization of device and relative relationship between outer suction catheter 22 and inner infusion catheter 24 under fluoroscopy to enter an epidural abscess 32 (FIGS. 10-12).

The outer suction catheter 22 is lined by PTFE 33 at its distal end has four openings 34 with a diameter of 0.025 inches each. The distal openings 34 (FIGS. 4-6) are placed 0.075 inches from the distal end 23 of suction catheter 22. The proximal openings 34 are placed 0.15 inches from the distal most end 23 of suction catheter 22. The inner infusion catheter 24 PTFE-lined polyimide is designed the have a length of 100 cm. The outer diameter is 0.026 inches and inner diameter is 0.016 inches. The infusion catheter 24 has a single lumen with a distal port 25 and proximal port 25a.

Figure 13:
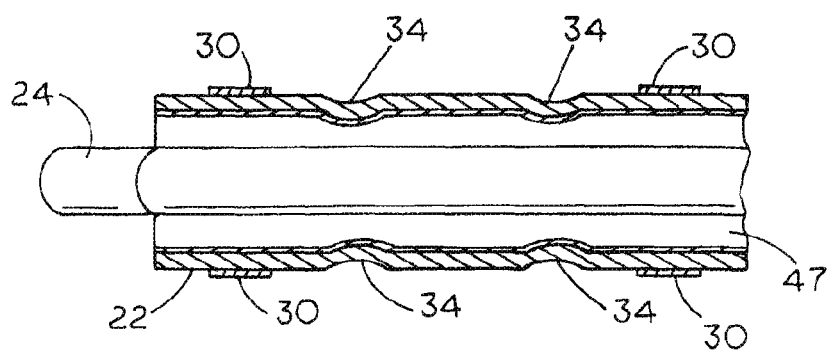
FIG. 13 shows a modification of the inner infusion catheter equipped with a pressure driven closure valve placed at the distal end of the inner infusion catheter.
Figure 14:
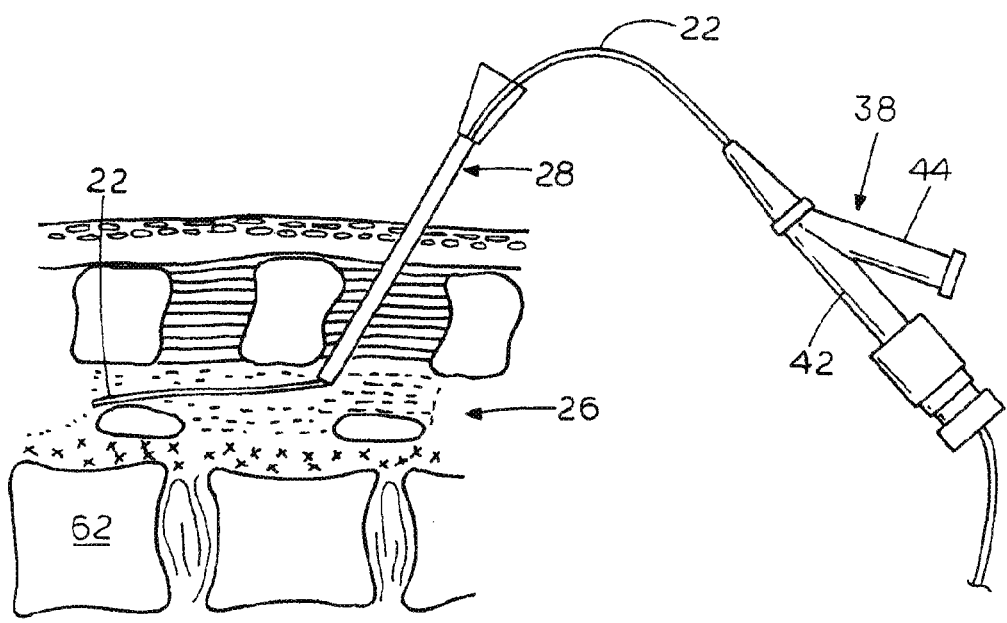
FIG. 14 demonstrates the use of a guidewire to direct the drainage catheter through the needle into the extradural space in a longitudinal also identifying the distal end of the guidewire which can be manipulated by rotation of the proximal end of the guidewire.
Figure 15:
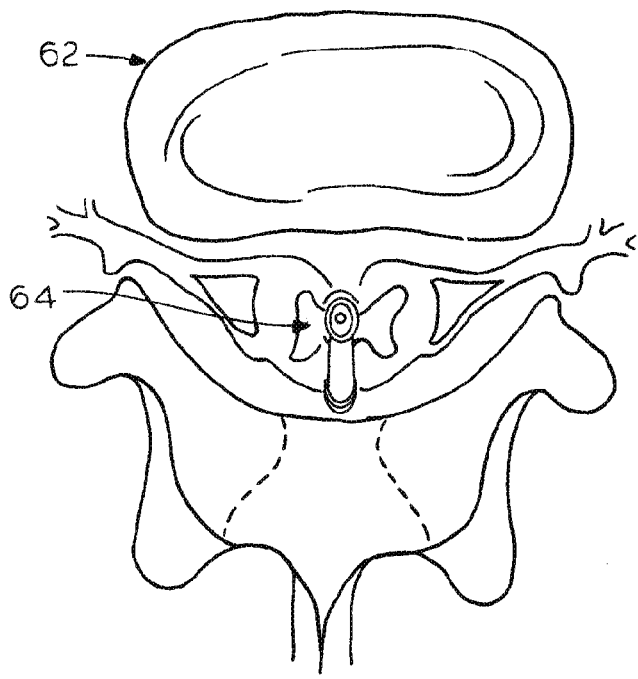
FIG. 15 is a cross-sectional view showing a spinal cord illustrating the relationship between the outer suction catheter and spinal cord, extradural space and vertebral body.
Figure 16A:
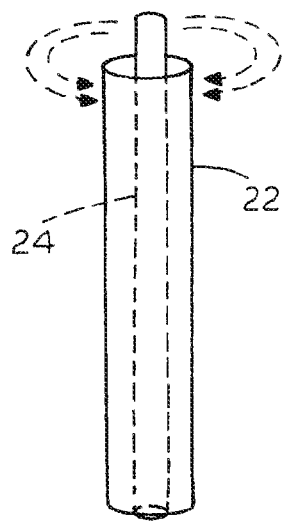
FIGS. 16A-16D are longitudinal views of various positions of the inner infusion catheter in relation to the outer suction catheter that demonstrates changes in trajectory of fluid motion from infusion to aspiration by various lengths and angulations of protrusion of the inner infusion catheter.
Figure 16B:
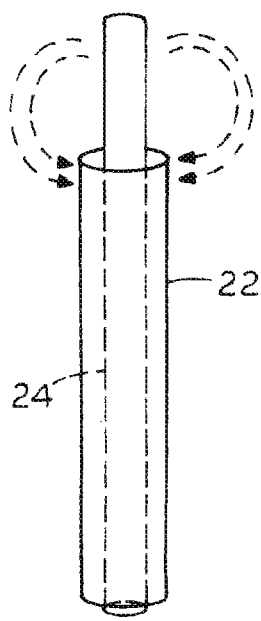
Figure 16C:
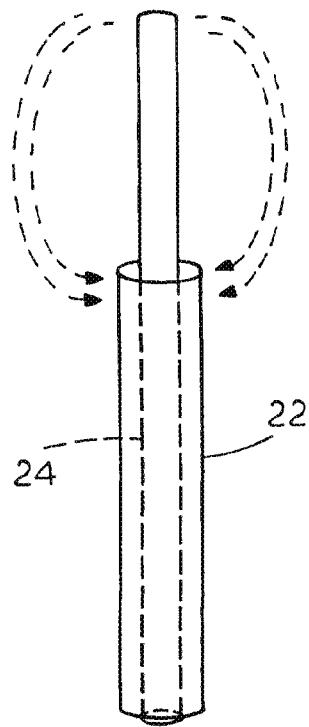
Figure 16D:
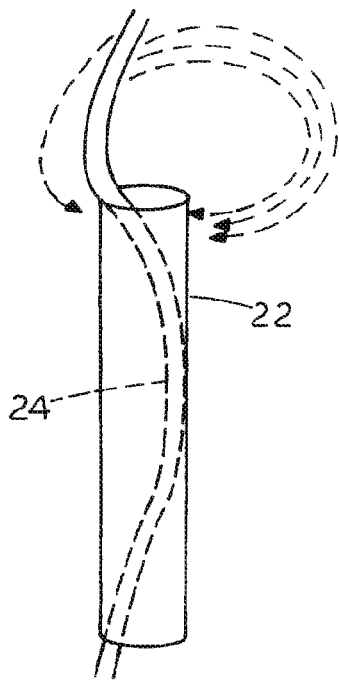

The device is designed to be advanced in a cephalad direction through the extradural space 26 under fluoroscopic guidance (FIGS. 8, 9 and 15) by manually pushing and rotating the proximal ends of both the catheters. A guidewire 36 can be introduced through the central lumen of infusion catheter 24 and used to navigate the device through the extradural space 26 to a target location (FIG. 13). The device enters the epidural abscess 32 with the inner infusion catheter 24 leading, followed closely by the outer suction catheter 22 (FIG. 10). Once the device is in place within the epidural abscess 32, the proximal port of the inner infusion catheter 24 is connected to an infusion system 40 that infuses normal saline or water in a continuous or pulsatile spray mode (FIGS. 11 and 12). The proximal portion of the outer suction catheter 22 is attached to a two-way Y connector 38. The central port 42 of the Y connector 38 provides access to the infusion catheter 24 and angulated port 44 is designed to be connected to a suction pump 46.

The infusion of normal saline or water can be initiated in a continuous or pulsatile spray mode. The infusion system 40 (FIGS. 11 and 12) can be set to a particular volume (range 1-5 cc per minute) and particular pressure (range 10-30 cm of $H_2O$) above which the infusion will automatically discontinue (FIG. 12). Simultaneous suction is initiated by the suction pump 46 at suction pressures ranging from −5 to −30 cm of $H_2O$. The suction can be continuous or may be synchronized with the infusion system 40 to follow each infusion pulse or blast. The aspirated material moves to the exterior of the device (FIG. 11) through the space between the outer suction catheter 22 and inner infusion catheter 24, which forms a suction conduit 47 which leads into the angulated proximal end of the outer suction catheter 22 when the material is subsequently collected in a transparent suction bag 48 that allows continuous visual monitoring and assessment of quantity and quality of aspirate.

The suction process is continued until no further purulent material is observed in the aspirate from the suction catheter 22 entering the bag 48. Subsequently, a stepwise withdrawal of the inner infusion catheter 24 under continued suction by the outer suction catheter 22 is performed. The outer catheter is withdrawn from the extradural space 26 under suction to avoid leakage of any residual purulent material. The introduction needle is removed allowing a spontaneous seal of the insertion site.

In the drawings, the intervertebral foramen is shown at 60, vertebral bodies at 62 and the spinal cord at 64.

In one modification of the inner infusion catheter 24, a pressure driven closure valve 50 is constructed at the distal end of the inner infusion catheter 24 by providing a 2 mm segment that is made of polyurethane and collapsible. The valve 50 (FIGS. 17A and 17B) is designed to slow or stop the infusion if the localized pressure in the vicinity of the distal end of the inner infusion catheter 24 exceeds 25 mm Hg.

As will be appreciated, the procedure and device represent a new method consisting of using an infusion suction catheter and introducer sheath inserted through a percutaneous entry in extradural space from the lumbar region with advancement and manipulation in the extradural space using radiographic (fluoroscopic) guidance. The system provides a combination of infusion and aspiration to drain epidural abscesses with specific indications to treat epidural abscesses involving the high cervical region (C4 or higher); epidural abscess extending to three levels or more; epidural abscess with concurrent involvement of any vertebral body at the level of abscess; epidural abscess with evidence of concurrent spinal axis instability (sublaxation, deformity, loss of intervertebral disc space, kyphosis, or spondolithetiasis).

The distal end of the infusion catheter is closed off and rounded using a die with shaft material which reflows and closes off the end using radiofrequency energy. The infusion catheter is preferably made of 55D Pebax with ensures that the tip is flexible for maneuvering and does not damage the dural membranes. The infusion catheter can be manipulated in the vicinity of concurrent spinal axis instability without placing additional strain on the spinal axis.

The pressure driven closure valve placed at the distal end of the inner infusion catheter includes a 2 mm segment that is made of polyutherane and collapsible and will slow or stop the infusion if the localized pressure in the vicinity of the distal end of the inner infusion catheter exceeds about 25 mm Hg. Such a mechanism prevents worsening of new compression on spinal cord by excessive pressure build up within the extradural space.

The size and shape of the distal end of the aspiration catheter of the invention is uniquely adapted to enable aspiration of high viscosity purulent material without applying suction to the membranes. The distal end of the infusion catheter which is placed inside the suction catheter but protrudes out at the distal end of the suction catheter deflects the axis of suction away from the dural membranes towards the extradural space. There is no suction at an angulation to the axis of the suction.

FIGS. 16A-16D depict longitudinal views showing both the outer aspiration catheter 22 and inner infusion catheter 24 in various relationships and illustrating the highly maneuverable nature of the inner infusion catheter with respect to the outer catheter. This enables more precise fluid motion trajectories from infusion to aspiration to be used with regard to various abscesses to be addressed.

Figure 17A:
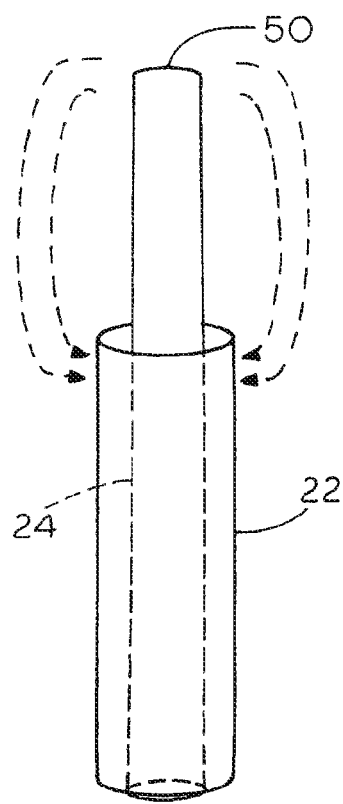
FIGS. 17A and 17B demonstrate the compressible aspect of inner infusion catheter that prevents any further infusion under excess external pressure prevents thus avoid dangerous levels of infusion and pressure buildup within the epidural compartment.
Figure 17B:
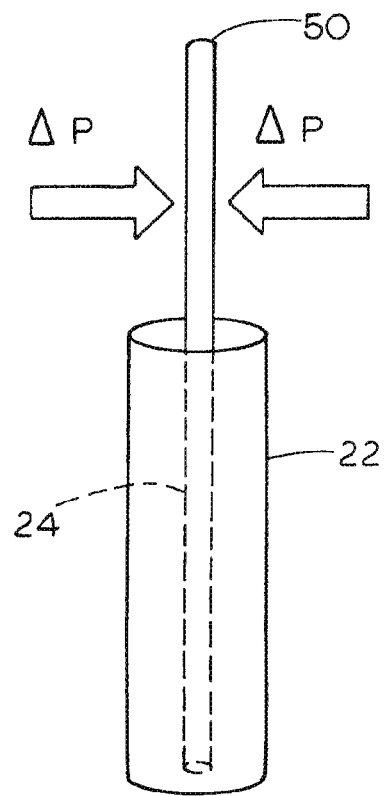

FIGS. 17A and 17B illustrate the effect of excess external pressure on the infusion catheter in which infusion/aspiration in FIG. 17A is normal, but with excess pressure in FIG. 17B, the infusion catheter collapses and no longer infuses solution into the patient.

A 6F introducer sheath that can be placed percutaneously into the epidural space. It has a 55D Pebax with SST coil running entire length for kink resistance and PTFE liner for lubricity. The introducer sheath allows access to the epidural space for prolonged periods in various positions without damaging the tissue unlike the needle. The introducer sheath can enable a user to introduce and withdraw infusion and suction catheters without losing access to the epidural space.

The radio-opaque marker bands on distal ends of outer suction catheter and inner infusion catheter allow fluoroscopic assessment of the relative position of distal end of both catheters. The radio-opaque markers also enable manipulation of the catheters within the epidural space under fluoroscopic guidance and accurate placement within the abscess.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A minimally invasive method of aspirating purulent material from an epidural abscess in a patient comprising:
   (a) providing a dual concentric catheter system having an inner infusion catheter having a pressure driven closure valve and an outer suction catheter having a plurality of side openings, wherein said infusion catheter is able to be independently axially adjusted relative to the outer suction catheter and thereby advanced relative to and beyond said suction catheter a variable desired distance as necessary during a procedure, said infusion catheter having a blunt tip of flexible material;
   (b) introducing said dual concentric catheter systems into an extradural space through percutaneous entry employing a needle followed by an introducer sheath in extradural space and advancing it along the extradural space of a patient to an epidural abscess of interest using radiographic guidance, the inner infusion catheter being advanced over a guidewire beyond the outer suction catheter;
   (c) infusing flushing liquid material into said epidural abscess from a distal portion of said infusion catheter in a manner that causes purulent material to be dislodged toward said side openings in said suction catheter and removing purulent material by aspiration through said side openings in said suction catheter and a suction conduit between the inner and outer catheters until no purulent material is observed in the aspirate;
   (d) allowing said pressure driven closure valve placed at a distal end of the inner infusion catheter in the form of a collapsible segment to slow or stop the infusion process if a localized pressure in the vicinity of the distal end of the inner infusion catheter exceeds a given value, wherein the given value is 25 mm Hg; and
   (e) withdrawing said dual catheter system from said extradural space.

2. A method as in claim 1 including maneuvering said inner infusion catheter axially beyond the outer suction catheter, thereby allowing changes in trajectory of fluid motion from infusion to aspiration by various lengths and angulations of protrusion of the inner infusion catheter.

3. A method as in claim 1 wherein said flushing liquid is selected from saline and other compatible materials.

4. A method as in claim 1 including monitoring the position of the catheter system and the relative position of distal ends of said inner infusion and outer suction catheters using fluoroscopic imaging to identify radio-opaque marker bands on the distal end of both catheters and advancing said system through said abscess and maneuvering and positioning said inner infusion catheter during aspiration.

5. A method as in claim 1 wherein said dual catheter system is advanced over a guidewire.

6. A method as in claim 1 wherein said dual concentric catheter system is introduced through a percutaneous needle and introducer sheath and advanced over a guidewire after removal of the needle.

7. A method as in claim 1 further comprising controlling aspiration suction and synchronizing aspiration suction with infusion which is administered in a manner selected from continuous and pulsed spray modes.

* * * * *